(12) United States Patent
Ran

(10) Patent No.: US 7,063,723 B2
(45) Date of Patent: Jun. 20, 2006

(54) INTRAOCULAR LENS WITH AN ACCOMMODATING CAPABILITY

(76) Inventor: Sun Ran, 423 Edgebrook Grove, Calgary, Alberta (CA) T3A 5T4

( * ) Notice: Subject to any disclaimer, the term of this patent is extended or adjusted under 35 U.S.C. 154(b) by 0 days.

(21) Appl. No.: 10/710,607

(22) Filed: Jul. 23, 2004

(65) Prior Publication Data
US 2006/0020339 A1    Jan. 26, 2006

(51) Int. Cl.
A61F 2/16 (2006.01)
(52) U.S. Cl. .................. 623/6.37; 623/6.39; 623/6.4
(58) Field of Classification Search ....... 623/6.37–6.47
See application file for complete search history.

(56) References Cited

U.S. PATENT DOCUMENTS

| | | |
|---|---|---|
| 4,409,691 A | 10/1983 | Levy |
| 4,463,457 A * | 8/1984 | Kelman ............... 623/6.43 |
| 4,787,903 A | 11/1988 | Grendahl |
| 4,790,847 A | 12/1988 | Woods |
| 4,816,031 A | 3/1989 | Pfoff |
| 4,888,012 A * | 12/1989 | Horn et al. .......... 623/6.13 |
| 4,892,543 A | 1/1990 | Turley |
| 4,932,966 A | 6/1990 | Christie et al. |
| 4,994,082 A | 2/1991 | Richards et al. |
| 5,108,429 A | 4/1992 | Wiley |
| 5,171,266 A | 12/1992 | Wiley et al. |
| 5,275,623 A | 1/1994 | Sarfarazi |
| 5,443,506 A | 8/1995 | Garabet |
| 5,489,302 A | 2/1996 | Skottum |
| 5,496,366 A | 3/1996 | Cumming |
| 5,674,282 A | 10/1997 | Cumming |
| 5,843,188 A | 12/1998 | McDonald |
| 6,013,101 A | 1/2000 | Israel |
| 6,152,958 A * | 11/2000 | Nordan ............... 623/6.25 |
| 6,200,342 B1 | 3/2001 | Tassignon |
| 6,231,603 B1 | 5/2001 | Lang et al. |
| 6,443,985 B1 * | 9/2002 | Woods ............... 623/6.46 |
| 6,533,813 B1 | 3/2003 | Lin et al. |
| 6,596,026 B1 | 7/2003 | Gross et al. |
| 6,645,245 B1 | 11/2003 | Preussner |
| 6,863,687 B1 * | 3/2005 | Sun et al. .......... 623/6.46 |
| 2002/0128710 A1 | 9/2002 | Eggleston |
| 2003/0083744 A1 | 5/2003 | Khoury |
| 2004/0111152 A1 * | 6/2004 | Kelman ............... 623/6.37 |

* cited by examiner

*Primary Examiner*—Suzette J-J Gherbi
(74) *Attorney, Agent, or Firm*—Bennett Jones LLP

(57) ABSTRACT

An introocular lens (IOL) includes an optic; a haptic; a flexible membrane substantially encircling the optic and connected between the optic and the haptic, the flexible membrane having a flexibility greater than the optic and the haptic. The flexible membrane permits travel of the optic relative to the haptic to permit accommodation in the eye. The flexible membrane my also drive a curvature change in the optic as it travels during accommodation.

26 Claims, 4 Drawing Sheets

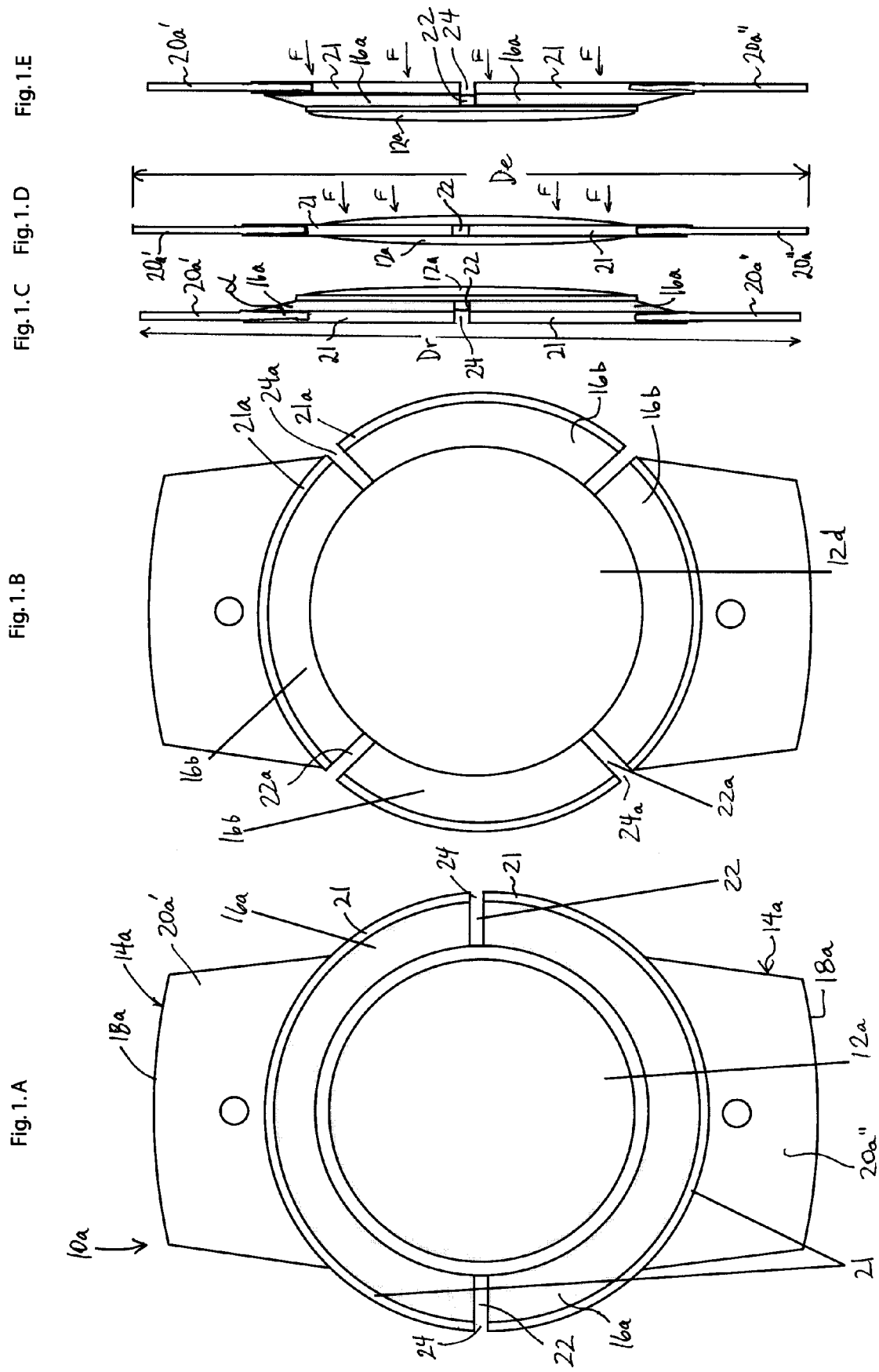

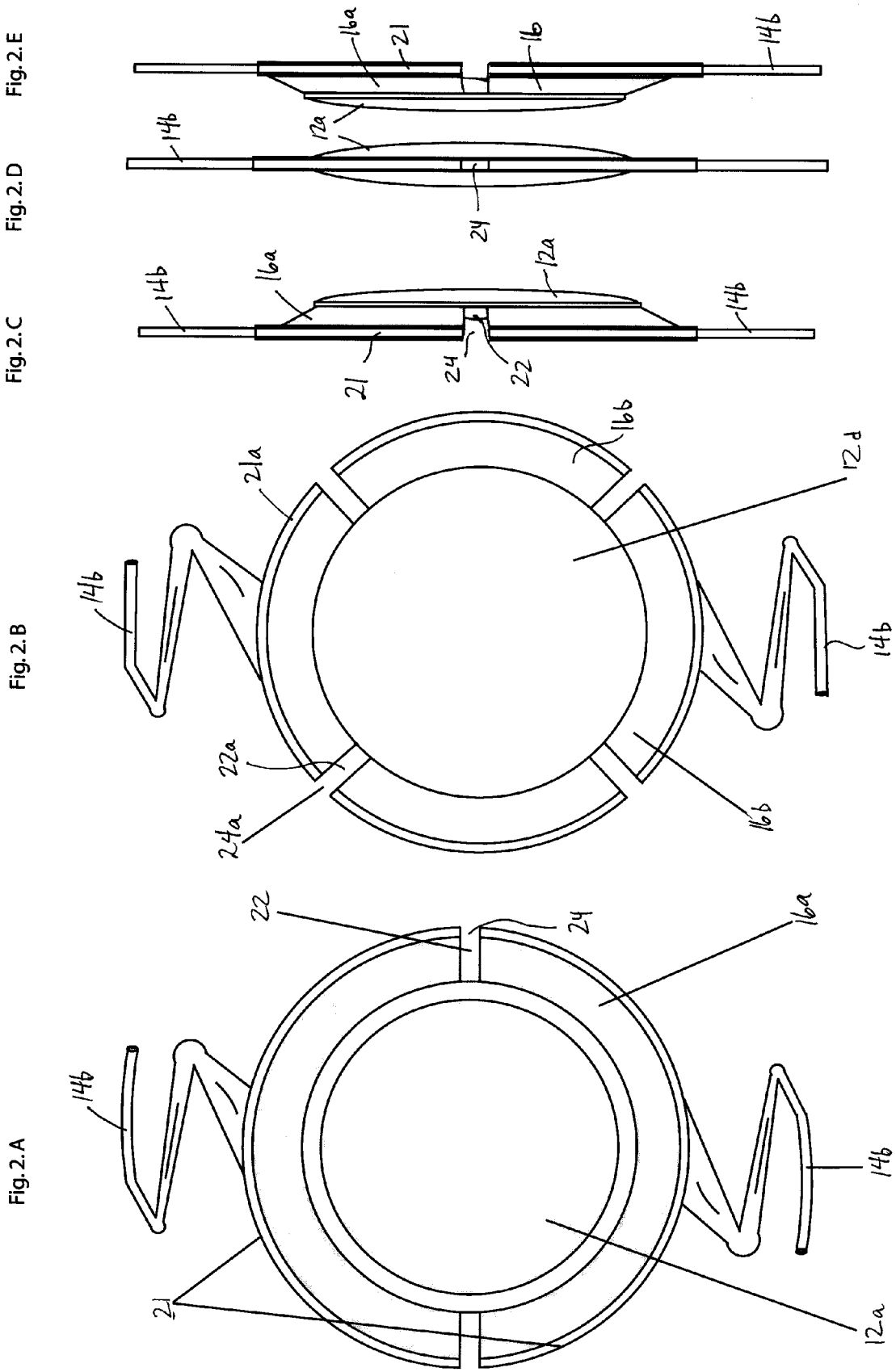

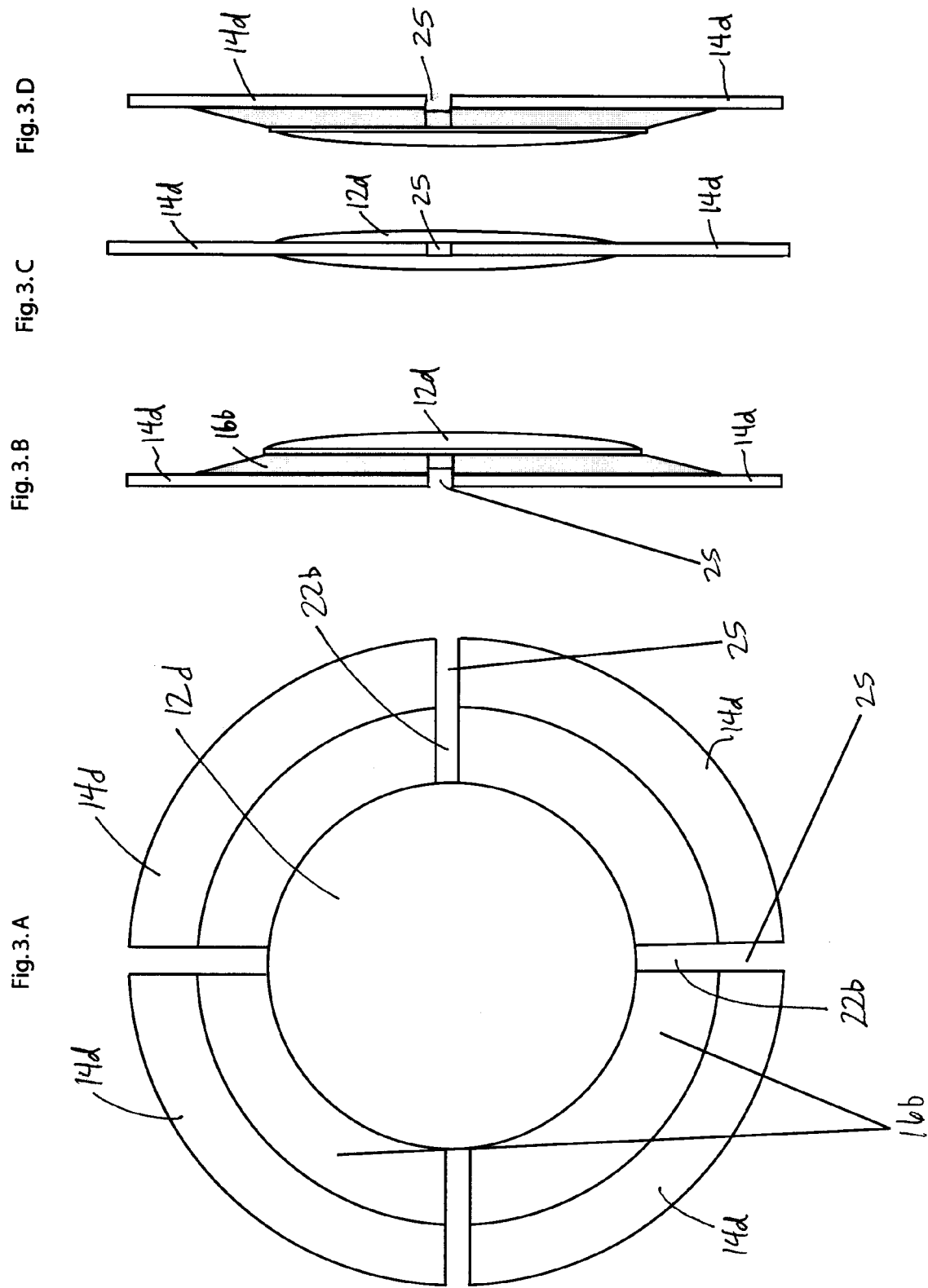

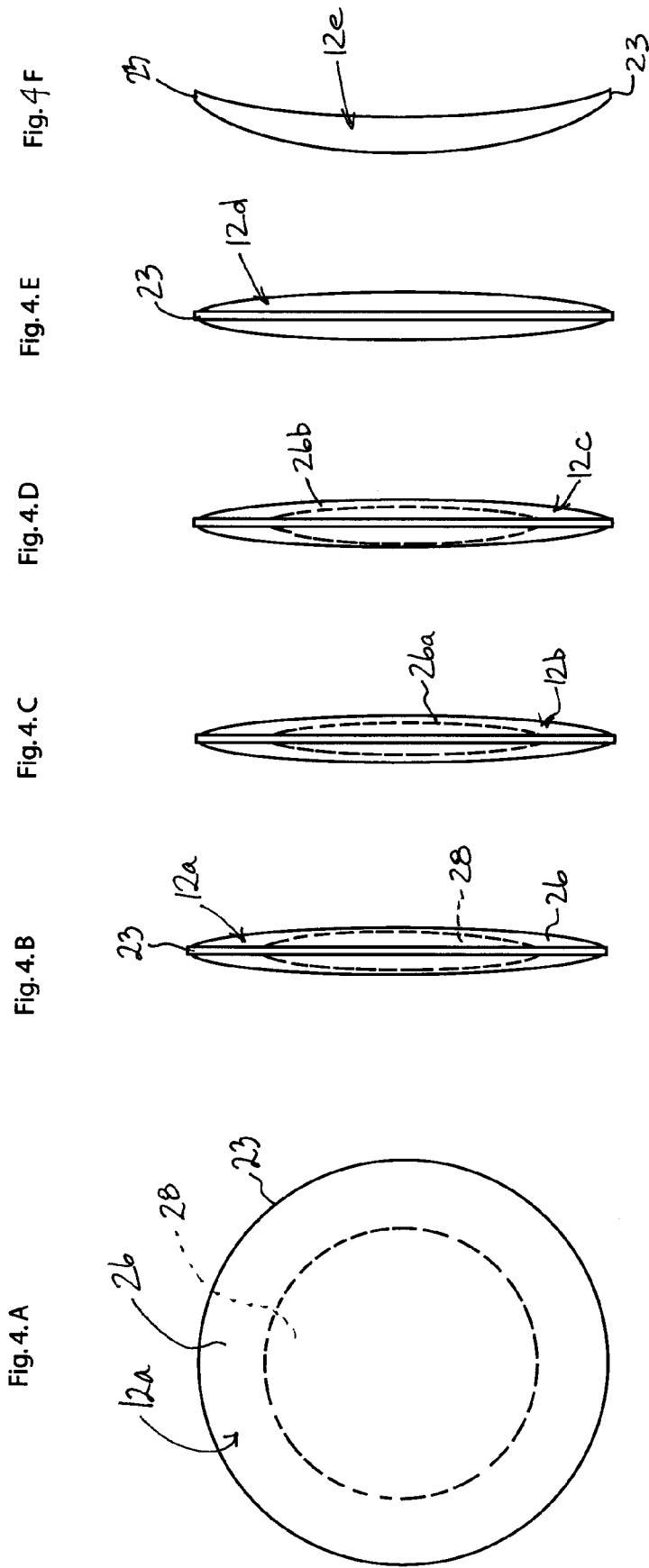

INTRAOCULAR LENS WITH AN ACCOMMODATING CAPABILITY

BACKGROUND OF INVENTION

The present invention relates generally to an intraocular lens and, in particular, an intraocular lens with accommodating capability.

An intraocular lens (IOL) is a surgical device, which can be implanted into the eye to replace cloudy natural lens during cataract surgery. However, the artificial lens is different from the natural lens, which can change shape to facilitate accommodation of the eye. Therefore, almost every patient needs reading glasses for near work after cataract surgery.

IOLs are known with accommodating capabilities. Currently, a number of different approaches have been attempted for designing an accommodating IOL, such as forward movement of lens optic, curvature change of the lens optic, and change of refractive index of the lens optic.

SUMMARY OF INVENTION

In accordance with a broad aspect of the present invention there is provided an IOL comprising: an optic; a haptic; a flexible membrane substantially encircling the optic and connected between the optic and the haptic. The flexible membrane has a flexibility greater than the optic and greater than the haptic.

BRIEF DESCRIPTION OF DRAWINGS

FIG. 1A is front elevation of an intraocular lens.

FIG. 1B is front elevation of another intraocular lens.

FIGS. 1C to 1E are side elevations of the intraocular lens of FIG. 1A showing its positions during accommodation, wherein FIG. 1C is at rest and FIGS. 1D and 1E are undergoing accommodation by forward movement of the lens optic.

FIG. 2A is front elevation of another intraocular lens.

FIG. 2B is front elevation of another intraocular lens.

FIGS. 2C to 2E are side elevations of the intraocular lens of FIG. 2A showing its positions during accommodation, wherein FIG. 2C is at rest, FIG. 2D is at a stage of accommodation and FIG. 2E is at a further stage of accommodation.

FIG. 3A is front elevation of another intraocular lens.

FIGS. 3B to 3D are side elevations of the intraocular lens of FIG. 3A showing its positions during accommodation, wherein FIG. 3B is at rest and FIGS. 3C and 3D are at progressive stages of accommodation.

FIGS. 4A and 4B are front and side elevations, respectively, of lens optics useful in the present invention.

FIGS. 4C to 4F are side elevations of further lens optics useful in the present invention.

DETAILED DESCRIPTION

In one embodiment, an IOL may provide accommodating capability by forward movement in the eye, varying the distance of the IOL or lens optic from the retina, and/or curvature change of the lens optic. To achieve these affects, the IOL may make use of the forces of zonule tension from ciliary muscle contractions. In addition, vitreous forces may act upon the IOL. Vitreous forces are also reliant, at least in part, on ciliary muscle contractions wherein such contractions result in posterior bulking within the eye, which decreases the volume of the vitreous cavity. Since the vitreous volume is fixed, the pressure on the contraction of the ciliary muscle cause vitreous movement wherein the peripheral vitreous is pushed back and the central vitreous moves oppositely and, therefore, forwardly. Consequently, the movement of the vitreous may push the lens optic forward in the eye. It appears that forward movement of the lens optic must be significant in order to adjust the lens power for example to provide near vision. However, minor curvature changes on the lens optic appear to change the lens power significantly.

An IOL providing accommodation by forward movement in the eye and/or curvature change of the lens optic is shown in FIGS. 1A and 1C to 1E. In one embodiment, an IOL 10a includes a lens optic 12a and a haptic 14a. As is known, lens optic 12a provides for the corrective refraction of light for focusing to the retina, while haptic 14a is a supporting structure for mounting the optic in the capsular bag. Haptic 14a includes mounting points 18a, which engage against the capsular bag.

The lens optic is secured to the haptic through flexible, elastomeric membranes 16a. Membranes 16a together at least substantially encircle optic 12a. Each membrane has a flexibility greater than that of the surrounding materials. In particular, each membrane 16a has a flexibility greater than that of either lens optic 12a or haptic 14a. Flexibility may be achieved by selection of materials or, as in the illustrated embodiment, by selection of the thickness of the membrane relative to the surrounding parts. For example, the membranes may be formed thinner and possibly much thinner than the haptic to render it more flexible than that part. While two membranes are shown, it is to be understood that one substantially circular membrane may be employed, if desired. Alternately, further membranes may be positioned such that they together encircle optic 12a. For example, with reference to FIG. 1B, an IOL is shown including four membranes 16b about optic 12a.

The membranes are able to flex to permit movement of optic 12a relative to haptic 14a, in response to the application of force to optic 12a. The membranes, however, are resilient such that they are biased towards their original form as the application of force is diminished or discontinued.

Haptic 14a may be formed in various ways to mount the IOL in the posterior chamber or the anterior chamber of an eye and to support the membranes 16a and therethrough lens optic 12a. While other haptic forms can be used as desired, in the illustrated embodiment, haptic 14a is a plate haptic including an upper half 20a' and a lower half 20a". The haptic includes a membrane support ring formed of segments 21. In particular, each of the upper half and the lower half of the haptic includes a ring segment 21 that extends the haptic upwardly around the optic to support membranes 16a. In the illustrated embodiment, ring segments 21 frame the membranes 16a to offer support for the membranes at their outer edges. Ring segments 21 may be formed as a part of the haptic or sepearately therefrom with a connection to the haptic.

Membranes 16a may be mounted at or close to the optic's largest diameter side edges 23 (see FIG. 4) and each membrane extends along a section of the circumference about the optic such that membranes 16a together substantially encircle the optic. The membranes may be independent from each other, for example in one embodiment separated by slits or gaps 22. In the illustrated embodiment, the IOL includes two membranes 16a about the optic, with each membrane being continuous between its ends and extending substantially about one half the optic circumference. The membranes are spaced apart at each of their ends to form gaps 22 therebetween. The gaps may, for example, be positioned on the sides of the IOL between the haptic mounting points 18*a*.

Haptic 14*a* may also be discontinuous, for example by forming the upper half 20*a*' separate from the lower half 20*a*", for example, at a split or gap 24 adjacent to gaps 22 between membranes 16*a*.

Gaps 22 and 24 reduce stiffness and resistance to bending for the IOL wherein only the optic provides stiffness between the upper half and the lower half of the haptic. As such, when the ciliary muscle contracts to change the zonule tension and increase the vitreous pressure, the IOL can easily bend between gaps 22 and 24. Furthermore, where gaps 22, 24 are used that space the surrounding parts, the gaps can allow for greater range of motion to facilitate depth movement of the optic as the parts do not readily bear against each other. Gaps 22, 24 also permit dimensional expansion of the IOL wherein the diameter $D_r$ of the IOL at rest (FIG. 1C) may be extended to diameter $D_e$ wherein the IOL is expanded about gaps 22, 24 (FIG. 1D). The expansion to diameter $D_e$ facilitates travel of optic 12*a* to thereby facilitate accommodation.

In an IOL having more than two membranes, as in FIG. 1B, gaps 22*a*, 24*a* may be formed between each membrane 16*b* and between each ring segment 21*a*. The ring segments 21*a* may be extended about the membranes 16*b* to support them on their outer edges.

The surface area of optic 12*a* and membranes 16*a* also act to trap vitreous fluid as it is moved within the eye by ciliary muscle contractions. The form of membranes 16*a* act to trap the fluid pressure and this creates a force, arrows F, that acts with the flexibility of membranes 16*a* to drive forward movement of the optic.

In operation, when the ciliary muscle contracts, vitreous pressure will increase and act on the posterior surface area of the lens optic and membranes 16*a* to push the lens optic forward as shown progressively from FIG. 1C where the IOL is at rest through the position of FIG. 1D to the position of FIG. 1E. In addition, such movement of optic 12*a* and membranes 16*a* changes the pressure exerted at side edges 23 of the optic by the membranes. This causes the optic curvature to be changed. When the ciliary muscle relaxes, the vitreous pressure is released and the lens optic will return to its original form (FIG. 1C) and position because of material elasticity. A combination of forward movement and lens optic curvature change may provide the eye with significant accommodating power to focus on near objects.

The membranes can be formed at an angle to the optic to enhance their effect on optic curvature change when force is applied thereto. In one embodiment, the membranes together form a frustoconical surface formed at an angle $\alpha$ of 5 to 15 degrees or possibly 10 to 15 degrees from a plane defined through the optic side edges 23. An increase in angle $\alpha$ increases the degree to which optic 12*a* can travel. Consequently, it may add more positive power for near vision.

The IOLs can be made from various materials, as would be appreciated by a skilled person. For example, the materials for the optic and possibly for other parts are clear and compatible for use in the body. The materials are selected and formed to be sufficiently stiff to retain the IOL form and position in the eye, but to be flexible to react to muscle contractions and vitreous fluid pressure. Where a foldable lens is useful, foldable materials such as silicone, acrylic, hydrogel, etc. may be used. One-piece construction may also be useful. In the illustrated embodiment a one-piece construction is used wherein the haptic, ring segments, membranes and optic are formed integral.

Lens optics useful in the present invention may vary, as desired. For example, a liquid form optic, as shown in FIGS. 1A and 2A, or a solid form optic 12*d*, as shown in FIGS. 1B, 2B and 3A can be selected for the lens optic. Some useful optic forms are shown in FIG. 4. For example, as shown in FIGS. 4A and 4B, a liquid lens optic 12*a* may be used. Such a lens optic may include an outer capsule 26 forming an inner chamber 28 that may be filled with liquid material such as silicone or other liquid and clear materials. The lens capsule may be thinned centrally with an increasing peripheral thickness, as shown in FIG. 4B. In other embodiments, a lens optic 12*b* may be used wherein the lens capsule 26*a* may be more uniformly thick (FIG. 4C), a lens optic 12*c* may be used wherein the lens capsule 26*b* can include one thicker side (FIG. 4D). Capsule design can be selected to control lens optic shape change and thereby curvature changes resulting from application of pressure. A liquid lens tends to have greater flexibility of a solid lens. Solid optics may include, for example, an optic 12*d* (FIG. 4E) including a form generally symmetrical about its edges 23 or an optic 12*e* (FIG. 4F) that is curved assymetrically on either side of its side edges 23. If a solid optic is selected, soft and flexible materials may be used to construct the optic in order to facilitate curvature change.

It is to be understood that while a particular haptic form is shown, other haptic forms may be used as desired such as, for example, as shown in FIGS. 2A to 2D, a frog leg form haptic 14*b*, such as is disclosed in applicant's corresponding U.S. patent application Ser. No. 10/248,917 or a running leg form, also disclosed in the aforementioned patent application. In another embodiment, an alternate plate form, known as a pie shaped haptic 14*d* may be used such as is shown in FIGS. 3A to 3D. In an IOL having a pie shaped haptic, membranes 16*b* are mounted along their outer edges to haptic 14*d*. Gaps 22*b* may be provided between the membranes and gaps 25 may be formed in the haptic adjacent gaps 22*b* to provide the flex about gaps described hereinabove. Although not shown, a ring may be positioned or formed between membranes 16*b* and haptic 14*d*, if desired, for additional support of the membranes.

It will be apparent that many other changes may be made to the illustrative embodiments, while falling within the scope of the invention and it is intended that all such changes be covered by the claims appended hereto.

The invention claimed is:

1. An IOL comprising:
   a liquid form optic;
   a haptic;
   a flexible membrane substantially encircling the optic and connected between the optic and the haptic to space the haptic from the optic, the flexible membrane having a flexibility greater than the optic and greater than the haptic.

2. The IOL of claim 1 wherein the membrane is discontinuous about the optic.

3. The IOL of claim 1 wherein the membrane is formed of a plurality of membranes each extending along a section of the circumference about the optic such that the plurality of membranes together substantially encircle the optic.

4. The IOL of claim 3 wherein the plurality of membranes are independent from each other.

5. The IOL of claim 3 including gaps formed between at least some of the plurality of membranes.

6. The IOL of claim 1 wherein the haptic is discontinuous about the optic.

7. The IOL of claim 5 wherein the haptic includes gaps adjacent the gaps of the membrane.

8. The IOL of claim 1 wherein the membrane is formed of two membranes each extending along a section of the circumference about the optic such that the two membranes together substantially encircle the optic.

9. The IOL of claim 1 wherein the membrane is formed of four membranes each extending along a section of the circumference about the optic such that the four membranes together substantially encircle the optic.

10. The IOL of claim 1 wherein the membrane is formed at an angle relative to a plane through the optic.

11. The IOL of claim 10 wherein the membrane forms a frustoconical surface tapering at an angle relative to the plane of the optic.

12. The IOL of claim 11 wherein the angle is between about 5 to 15 degrees.

13. The IOL of claim 1 wherein the membrane is supported by a support ring attached about the membrane's outer edges.

14. The IOL of claim 13 wherein the support ring is formed of segments.

15. The IOL of claim 1 wherein the haptic is plate shaped.

16. The IOL of claim 1 wherein the haptic is frog leg shaped.

17. The IOL of claim 1 wherein the haptic is pie shaped.

18. An IOL comprising:
an optic;
a haptic including a plurality of segments spaced apart at their ends forming spaces therebetween; and
a flexible membrane substantially encircling the optic and connected between the optic and the haptic to space the haptic from the optic, the flexible membrane having a flexibility greater than the optic and greater than the haptic and formed of a plurality of membranes each extending along a section of the circumference about the optic with gaps formed between at least some of the plurality of membranes such that the plurality of membranes together substantially encircle the optic; and
wherein the spaces of the haptic are positioned adjacent the gaps between the plurality of membranes.

19. The IOL of claim 18 wherein the plurality of membranes includes two membranes.

20. The IOL of claim 18 wherein the plurality of membranes includes four membranes.

21. The IOL of claim 18 wherein the optic is a solid form.

22. An IOL comprising:
an optic;
a haptic; and
a flexible membrane substantially encircling the optic and connected between the optic and the haptic, the flexible membrane having a flexibility greater than the optic and greater than the haptic and the flexible membrane being formed of four sub-membranes each extending along a section of the circumference about the optic such that the four sub-membranes together substantially encircle the optic.

23. The IOL of claim 24 wherein the optic is a solid form.

24. An IOL comprising:
an optic;
a haptic;
a flexible membrane substantially encircling the optic and connected between the optic and the haptic, the flexible membrane having a flexibility greater than the optic and greater than the haptic; and
a support ring attached about the flexible membrane's outer edges to support the flexible membrane, the support ring being formed of segments.

25. The IOL of claim 24 wherein the optic is a solid form.

26. The IOL of claim 24 wherein the support ring segments are positioned between slits in at least one of the flexible membrane and the haptic.

* * * * *